US008703432B2

(12) United States Patent
Rosander et al.

(10) Patent No.: US 8,703,432 B2
(45) Date of Patent: Apr. 22, 2014

(54) **RECOMBINANT *TREPONEMA* SPP. PROTEINS FOR USE IN VACCINE, ANTIBODIES AGAINST SAID PROTEINS, AND DIAGNOSTIC AND THERAPEUTIC METHODS INCLUDING THE SAME**

(75) Inventors: Anna Rosander, Uppsala (SE); Märit Pringle, Knivsta (SE)

(73) Assignee: Vicia Animal Health Science AB, Sollentuna (SE)

( * ) Notice: Subject to any disclaimer, the term of this patent is extended or adjusted under 35 U.S.C. 154(b) by 0 days.

(21) Appl. No.: 13/576,032

(22) PCT Filed: Jan. 28, 2011

(86) PCT No.: PCT/SE2011/050090
§ 371 (c)(1),
(2), (4) Date: Jul. 30, 2012

(87) PCT Pub. No.: WO2011/093783
PCT Pub. Date: Aug. 4, 2011

(65) Prior Publication Data
US 2013/0034560 A1    Feb. 7, 2013

Related U.S. Application Data

(60) Provisional application No. 61/298,960, filed on Jan. 28, 2010, provisional application No. 61/360,986, filed on Jul. 2, 2010.

(51) Int. Cl.
*G01N 33/53* (2006.01)
(52) U.S. Cl.
USPC ... 435/7.1; 424/184.1; 424/185.1; 424/190.1; 424/262.1
(58) Field of Classification Search
None
See application file for complete search history.

(56) References Cited

U.S. PATENT DOCUMENTS 6,096,323 A    8/2000  Walker et al.
6,287,575 B1   9/2001  Walker et al.

OTHER PUBLICATIONS

Schouls et al. Infection and Immunity. 1989, 57(9):2612.*
Colman et al. (Research in Immunology 145: 33-36, 1994.*
Houghten et al. (New Approaches to Immunization, Vaccines 86, Cold Spring Harbor Laboratory, p. 21-25, 1986.*
Accession No. P29721, Apr. 1, 1993 [online][retrieved on Mar. 30, 2011]Retrieved from EBI; Database Uniprot. <URL:http://srs.ebi.ac.uk|srsbin/cgi-bin/wgetz?-e+[uniprotid:TMPA_TREPH]|[uniprot-acc:TMPA_TREPH]+-noSession>.
Accession No. M58475, Aug. 1, 1991[online][retrieved on Apr. 1, 2011] Retrieved from EBI; Database EM_PRO <URL:http://www.ebi.ac.uk|Tools/es/cgi-bin/aligndisp.cgitool=epoefasta&jobid=fasta-2011 0401-07335774&annot=yes>.

Yelton, DB. et al., "*Treponema phagedenis* Encodes and Expresses Homologs of the *Treponema pallidum* TmpA and TmpB Proteins" In Infection and Immunity, Oct. 1991, vol. 59, No. 1 0, pp. 3685-3693.
Pringle M. et al., "Isolation and characterization of *Treponema phagedenis*-like spirochetes from digital dermatitis lesions in Swedish dairy cattle" In Acta Veterinaria Scandinavica, Oct. 2008, vol. 50.
Berry, Steven L. et al., "Field Evaluation of Prophylactic and Therapeutic Effects of a Vaccine Against (Papillomatous) Digital Dermatitis of Dairy Cattle in Two California Dairies", Proceedings of the 13th International Symposium and 5th Conference on Lameness in Ruminants, 2004.
Blowey, R.W. et al., "Digital Dermatitis in dairy cattle", Veterinary Record, vol. 122, pp. 505-508, May 1988.
Choi, B.K. et al., "Phylogenetic analysis of pathogen-related oral spirochetes.", Journal of Clinical Microbiology, vol. 34, No. 8, American Society for Microbiology, pp. 1922-1925, Aug. 1996.
Choi, B.K. et al., "Spirochetes from Digital Dermatitis Lesions in Cattle Are Closely Related to Treponemes Associated with Human Periodontitis", International Journal of Systematic Bacteriology, vol. 47, No. 1, International Union of Microbiological Studies, pp. 175-181, Jan. 1997.
Demirkan, I. et al., "Serological Evidence of Spirochaetal Infections Associated with Digital Dermatitis in Dairy Cattle", The Veterinary Journal, vol. 157, Baillière Tindall, pp. 69-77, 1999.
Demirkan, I. et al., "Isolation and cultivation of a spirochaete from bovine digital dermatitis", Veterinary Record, vol. 145, pp. 497-498, Oct. 1999.
Demirkan, I. et al., "Isolation and characterisation of a novel spirochaete from severe virulent ovine foot rot", Journal of Medical Microbiology, vol. 50, The Pathological Society of Great Britain and Ireland, pp. 1061-1068, Apr. 2001.
Erdile, Lorne F. et al., "OspA lipoprotein of burgdorferi is a mucosal immunogen and adjuvant", Vaccine, vol. 15, No. 9, Elsevier Science Ltd., pp. 988-996, Great Britain, 1997.
Evans, Nicholas J. et al., "Three unique groups of spirochetes isolated from digital dermatitis lesions in UK cattle", Veterinary Microbiology, vol. 130, pp. 141-150, Great Britain, 2008.
Gupta R.B. et al., "A Study of the Etiology of Foot-Rot in Cattle", The Cornell Veterinarian, vol. 54, No. 1, pp. 66-77, New York, Jan. 1964.
Hillstrom, Anna et al., "Digital dermatit—en tickande bomb i svenska losdrifter", Svensk Veterinartidning, No. 1, 2005.
Keil, D.J. et al., "Serological and Clinical Response of Cattle to Farm Specific Digital Dermatitis Bacterins", Immtech, Kansas, 2002.
Klitgaard, Kirstine et al., "Evidence of Multiple *Treponema* Phylotypes Involved in Bovine Digital Dermatitis as Shown by 16S rRNA Gene Analysis and Fluorescence In Situ Hybridization", Journal of Clinical Microbiology, vol. 46, No. 9, American Society for Microbiology, pp. 3012-3020, Sep. 2008.

(Continued)

*Primary Examiner* — Oluwatosin Ogunbiyi
(74) *Attorney, Agent, or Firm* — Browdy and Neimark, PLLC (57) ABSTRACT

The present invention relates to proteins and/or fragments and derivatives thereof and their use as vaccines and in biotechnological methods. The vaccines particularly include immunogenic proteins in *Treponema* spp. isolated from digital dermatitis in cattle. The present invention further relates to antibodies raised against said proteins or fragments thereof, and the use of said proteins in diagnostic methods in which antibodies are detected as a sign of digital dermatitis in cattle.

3 Claims, 2 Drawing Sheets

(56) References Cited

OTHER PUBLICATIONS

Losinger, William C., "Economic impacts of reduced milk production associated with papillomatous digital dermatitis in dairy cows in the USA", Journal of Dairy Research, vol. 73, Proprietors of Journal of Dairy Research, pp. 244-256, United Kingdom, 2006.

Manske, Thomas et al., "Topical treatment of digital dermatitis associated with severe heel-horn erosion in a Swedish dairy herd", Preventative Veterinary Medicine, vol. 53, pp. 215-231, 2002.

Moter, Annette et al., "Fluorescence in situ hybridization shows spatial distribution of as yet uncultured treponemes in biopsies from digital dermatitis lesions", Microbiology, vol. 144, pp. 2459-2467, Great Britain, 1998.

Nordhoff, Marcel et al., "High prevalence of treponemes in bovine digital dermatitis—A molecular epidemiology", Veterinary Microbiology, vol. 131, pp. 293-300, 2008.

Read, Deryck et al., "Experimental Transmission of Papillomatous Digital Dermatitis (Footwarts) in Cattle", Veterinary Pathology, vol. 33, No. 5, pp. 479-632, 1996.

Read, Deryck H. et al., "Pathogenesis of experimental papillomatous digital dermatitis (footwarts) in cattle: Bacterial morphotypes associated with early lesion development", pp. 271, Switzerland, Sep. 1998.

Rodriguez-Lainz, Alfonso et al., "Case-control study of papillomatous digital dermatitis in southern California dairy farms", Preventative Veterinary Medicine, vol. 28, pp. 117-131, 1996.

Setubal, Joao C. et al., "Lipoprotein computational prediction in spirochaetal genomes", Microbiology, vol. 152, pp. 113-121, Great Britain, 2006.

Trott, Darren J. et al., "Characterization of *Treponema phagedenis*-Like Spirochetes Isolated from Papillomatous Digital Dermatitis Lesions in Dairy Cattle", Journal of Clinical Microbiology, vol. 41, No. 6, American Society for Microbiology, pp. 2522-2529, Jun. 2003.

Vink, W.D. et al., "Diagnostic assessment without cut-offs: Application of serology for the modelling of bovine digital dermatitis infection", Preventive Veterinary Medicine, vol. 92, pp. 235-248, 2009.

Walker, R.L. et al., "Spirochetes isolated from dairy cattle with papillomatous digital dermatitis and interdigital dermatitis", Veterinary Microbiology, vol. 47, pp. 343-355.

Walker, Richard L. et al., "Humoral response of dairy cattle to spriochetes isolated from papillomatous digital dermatitis lesions", American Journal of Veterinary Research, vol. 58, No. 7, pp. 744-748, Jul. 1997.

Yano, Takahisa, "Identification of candidate pathogens of papillomatous digital dermatitis in dairy cattle from quantitative 16S rRNA clonal analysis", Veterinary Microbiology, vol. 143, pp. 352-362, 2010.

* cited by examiner

RECOMBINANT TREPONEMA SPP. PROTEINS FOR USE IN VACCINE, ANTIBODIES AGAINST SAID PROTEINS, AND DIAGNOSTIC AND THERAPEUTIC METHODS INCLUDING THE SAME

The present invention relates to proteins and/or fragments and derivatives thereof and their use as vaccines and in biotechnological methods. The vaccines particularly include immunogenic proteins in *Treponema* spp. isolated from digital dermatitis in cattle. The present invention further relates to antibodies raised against said proteins or fragments thereof, and the use of said proteins in diagnostic methods in which antibodies are detected as a sign of digital dermatitis in cattle.

BACKGROUND

Digital dermatitis (DD) is a contagious claw disease causing lameness in cattle, most commonly seen in intensive dairy production. The disease was first described in 1974 in Italy. In Sweden the first herd with DD was described recently (Hillström and Bergsten, 2005) whereas previously only sporadic, atypical cases have been reported (Manske et al., 2002). There is a strong connection between wet/dirty claw environments and the occurrence of DD (Rodriguez-Lainz et al., 1996), for example in cubicle systems where accumulation of faeces and urine on the alleys is a typical hygiene problem. Besides being an animal welfare problem, economic losses due to reduced milk production and weight loss are associated with DD (Losinger, 2006).

The rapid response to antibiotic treatment of DD lesions strongly supports a bacterial cause. Many bacteria of different genera, such as *Treponema, Fusobacterium, Dichelobacter, Prevotella*, and *Porphyromonas* have been isolated from DD lesions and a polymicrobial cause is often discussed. However, there is strong circumstantial evidence that *Treponema* spp. are central in the aetiology of DD. As early as 1964 spirochetes were observed in smears from different variants of "foot-rot" manifestations in cattle (Gupta et al., 1964). Another early observation of spirochetes was made 1988 when DD was described for the first time in the UK (Blowey and Sharp, 1988). The first spirochete cultures from DD were reported 1995 (Walker et al., 1995). In histological preparations from DD lesions treponemes are found invading the deeper layers of epidermis (Moter et al., 1998). Additionally a humoral immune response against *Treponema* spp. has been demonstrated in infected cattle (Walker et al., 1997; Trott et al., 2003). Successful experimental transmission of the disease through inoculation with fresh scrapings from DD lesions was described in 1996 (Read and Walker, 1996). It was also confirmed by histopathology that spirochetes invaded the tissue 1-2 weeks after inoculation (Read et al., 1998).

Several phylotypes of *Treponema* can be present in the same lesion. Different phylotypes have been isolated from the same animal (Walker et al., 1995; Evans et al., 2008) and by cloning and sequencing of 16S rRNA genes, five different phylotypes were identified in a pooled sample from four cows (Choi et al., 1997). It has also been demonstrated by fluorescence in situ hybridization on biopsies from DD lesions that the distribution in the dermal layers differs between phylotypes (Moter et al., 1998). The *Treponema phagedenis*-like phylotype was located mainly in the stratum corneum and stratum spinosum. Some phylotypes have not yet been reported as cultured. Recently the *Treponema phagedenis*-like phylotype has been indicated in several studies to be a key agent in the pathogenesis of DD (Klitgaard et al. 2008, Nordhoff et al. 2008, Yano et al. 2009).

In countries where DD is widespread, footbaths containing antibiotics are often used. These footbaths rapidly become contaminated with faeces and dirt and hence function as large selective cultures of antibiotic resistant bacteria. In Sweden tetracyclines are used, but only for topical treatment of individual animals since on herd level footbaths with copper sulphate are recommended.

To date no commercial vaccine or serologic test for DD is available. A humoral response against *Treponema* spp. has been shown in cattle with DD and used for whole cell lysate ELISA investigations in research (Demirkan et al. 1999, Trott et al. 2003, Vink et al. 2009, Walker et al. 1997). Novartis produced a whole cell lysate DD vaccine (TrepShield) for the USA market for some years in the early 2000s (Berry et al. 2004, Keil et al. 2002).

Technologies and strategies for development of vaccines are described in i.a. Vaccine Design: Innovative Approaches and Novel Strategies (Caister Academic Press, 2011) and Vaccines: From Concept to Clinic: A Guide to the Development and Clinical Testing of Vaccines for Human Use (Informa Healthcare, 1998). The use of a recombinant protein as a vaccine is described in Erdile et al. 1997.

SUMMARY

The present invention aims at providing efficient methods for diagnosis of and immuno-protection against dermatitis in animals, particularly digital dermatitis in ruminants, as well as products for said purposes.

The present invention revolves around immunogenic proteins in *Treponema* spp. isolated from digital dermatitis in cattle, and more specifically to recombinant proteins.

In a first aspect, the present invention relates to isolated *Treponema phagedenis*-like proteins, TmpA, Ttm, and PrrA, with amino acid sequence according to SEQ ID NO: 2, SEQ ID NO: 4 or SEQ ID NO: 6, respectively, to fragments and derivatives thereof capable of inducing an immune response to *Treponema* spp., and to fragments and derivatives capable of binding to antibodies produced by a subject in an immune response against said protein, as further defined below.

In one embodiment of the invention, the *Treponema* proteins, and fragments and derivatives thereof, are recombinantly produced.

In one aspect, the invention relates to nucleic acid molecules encoding the proteins, fragments and derivatives according to the invention.

The invention also relates to the use of said proteins, fragments and derivatives thereof in veterinary medicine, specifically as a vaccine for prevention of digital dermatitis.

In a further aspect, the present invention provides a veterinary vaccine for protection against digital dermatitis comprising one or more of said recombinant proteins and/or active fragments thereof, and conventional and suitable adjuvants. Such a vaccine may or may not further include other *Treponema* immunogens or whole cell lysates of different *Treponema* spp. in a vaccine for a broader immune response.

According to another aspect, the present invention also relates to a method for prevention of digital dermatitis in animals comprising the step of administering said vaccine to an animal in need thereof.

According to a still further aspect, there is provided a method of detecting presence of antibodies against *Treponema* spp. in a sample in which said recombinant proteins and/or active fragments are used to detect the presence of antibodies against *Treponema* spp. in said sample.

According to a still further aspect, there is provided a method for diagnosis of digital dermatitis in an animal in which said recombinant proteins and/or active fragments are used to detect the presence of antibodies against *Treponema* spp. in an animal.

In one embodiment of said detection method or diagnostic method, said recombinant proteins and/or active fragments are used in an ELISA (Enzyme-Linked ImmunoSorbant Assay) method.

In one aspect, the present invention relates to antibodies raised against said immunogenic proteins, or immunogenic derivatives or fragments thereof. Such antibodies are useful in treatment of disease caused by *Treponema* spp. by way of passive immunization and also in various laboratory methods such as immunomagnetic separation of *Treponema* bacteria.

BRIEF DESCRIPTION OF THE FIGURE

FIG. 1: Enzyme-linked immunosorbant assay with recombinant *Treponema phagedenis*-like strain V1 immunogenic proteins TmpA, Ttm, and PrrA as antigens. The assays were performed with sera from eight dairy cows with acute digital dermatitis (black bars), two cows with no known history of digital dermatitis and five calves 6-7 months of age (gray bars). Horse-radish peroxidase (HRP) conjugated rabbit anti-bovine IgG antibodies (Sigma) (A) or monoclonal 22:26 anti-bovine IgG-HRP antibodies (Svanova Biotech AB) (B) were used as secondary antibodies. Corrected optical density (COD) was measured at 450 nm.

DEFINITIONS

An "immunogenic agent", or "immunogen", is capable of inducing an immunological response against itself on administration to a patient, optionally in conjunction with an adjuvant.

An "active fragment" or "active derivative" as used in the present specification is a fragment or derivative of a native immunogenic agent, capable of inducing an immunological response against said native immunogenic agent on administration to a patient, optionally in conjunction with an adjuvant. An active fragment or derivative comprises or mimics at least one "epitope" or "antigenic determinant".

A "binding fragment" or "binding derivative" as used in the present specification is a fragment or derivative of a native immunogenic agent, capable of immunospecific binding to antibodies produced by a subject in an immune response against said native immunogenic agent. A binding fragment or derivative comprises or mimics at least one "epitope" or "antigenic determinant".

A "derivative" of a protein may be a protein showing substantial sequence homology to the original protein. The sequence homology may be 50% identity or more, such as 65%, 80%, 85%, 90%, 95% or 99% identity in amino acid sequence. The substituted amino acids are preferably conservative substitutions. The substituted amino acids may be natural or non-natural amino acids.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996).

Antibodies that recognize the same epitope can be identified in a simple immunoassay showing the ability of one antibody to block the binding of another antibody to a target immunogen, or fragment or derivative thereof.

The term "antibody" refers to an intact antibody, or a binding fragment thereof. An antibody may comprise a complete antibody molecule (including polyclonal, monoclonal or chimeric), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136).

SEQUENCE LISTING

| SEQ ID NO | Type | Description |
| --- | --- | --- |
| 1 | DNA | TmpA homolog, complete coding sequence |
| 2 | Protein | TmpA homolog, protein |
| 3 | DNA | putative tail tape measure protein (Ttm), complete coding sequence |
| 4 | Protein | putative tail tape measure protein (Ttm), protein |
| 5 | DNA | putative proline-rich lipoprotein (PrrA), complete coding sequence |
| 6 | Protein | putative proline-rich lipoprotein (PrrA), protein |
| 7 | DNA | GSTtmpAF1 (fwd) |
| 8 | DNA | GSTtmpAR1 (rev) |
| 9 | DNA | GSTkallaF1 (fwd) |
| 10 | DNA | GSTkallaR1 (rev) |
| 11 | DNA | GSTPGKEEF1 (fwd) |
| 12 | DNA | GSTPGKEER1 (rev) |
| 13 | DNA | ImpactPGKEEF1 (fwd) |
| 14 | DNA | ImpactPGKEER1 (rev) |
| 15 | DNA | ImpactkallaF1 (fwd) |
| 16 | DNA | ImpactkallaR1 (rev) |
| 17 | DNA | primer SAsekv |

DETAILED DESCRIPTION

Further Outline of Aspects and Embodiments of the Invention

In one aspect the present invention relates to an isolated protein having the amino acid sequence according to SEQ ID NO: 2, SEQ ID NO: 4 or SEQ ID NO: 6, or fragments or derivatives thereof capable of inducing an immune response to said protein, or a fragment or derivative capable of binding to antibodies produced by a subject in an immune response against said protein. Said protein, fragment or derivate may be used in veterinary medicine, such as in prevention of a disease caused by *Treponema* spp., such as digital dermatitis.

In another aspect, the present invention relates to a method for treatment or prevention of a disease caused by *Treponema* spp. comprising administering to a subject isolated protein having the amino acid sequence according to SEQ ID NO: 2, SEQ ID NO: 4 or SEQ ID NO: 6, or a fragment or derivative thereof capable of inducing an immune response to said protein. Said method may be used for a disease such as digital dermatitis.

In a further aspect, the present invention relates to a pharmaceutical composition comprising an isolated protein having the amino acid sequence according to SEQ ID NO: 2, SEQ ID NO: 4 or SEQ ID NO: 6, or a fragment or derivative thereof capable of inducing an immune response to said protein, and optionally pharmaceutically acceptable adjuvants, carriers and/or diluents.

In yet another aspect, the present invention relates to a method for detecting the presence of antibodies against proteins from *Treponema* spp. in a sample, comprising the steps:
bringing said sample in contact with an isolated protein having the amino acid sequence according to SEQ ID NO: 2, SEQ ID NO: 4 or SEQ ID NO: 6, or a fragment or derivative thereof capable of binding to antibodies produced by a subject in an immune response against said protein; and
detecting antibodies binding to said protein, fragment or derivative.

A further aspect of the invention relates to a method for in vitro diagnosis of a disease caused by *Treponema* spp. comprising the steps:
obtaining a sample of body fluid or tissue from a subject;
bringing said sample in contact with an isolated protein having the amino acid sequence according to SEQ ID NO: 2, SEQ ID NO: 4 or SEQ ID NO: 6, or a fragment or derivative thereof capable of binding to antibodies produced by a subject in an immune response against said protein; and
detecting antibodies binding to said protein, fragment or derivative;
wherein the presence of antibodies binding to said protein, fragment or derivative is indicative of a disease caused by *Treponema* spp.

Said method may be used for a disease such as digital dermatitis.

A further aspect of the invention relates to an antibody, or binding fragment thereof, binding specifically to an isolated protein having the amino acid sequence according to SEQ ID NO: 2, SEQ ID NO: 4 or SEQ ID NO: 6.

Another aspect of the invention relates to a method for treatment or prevention of a disease caused by *Treponema* spp. comprising administering said antibody to a subject. Digital dermatitis is one example of such a disease.

A further aspect of the invention relates to a method for separation of *Treponema* bacteria from a sample, comprising the steps:
bringing said sample in contact with said antibody bound to a solid phase;
allowing said antibody to bind to *Treponema* proteins in said *Treponema* bacteria; and
separating said solid phase from said sample
thereby separating said *Treponema* bacteria from said sample.

In said method, the separation may be achieved by for example immunomagnetic separation.

Another aspect of the invention relates to a nucleic acid molecule encoding the protein, fragment or derivative according to the present invention. In one embodiment the nucleic acid molecule encoding the protein has a nucleotide sequence selected from the group consisting of SEQ ID NO: 1, SEQ ID NO: 3, SEQ ID NO: 5 and parts thereof.

A further aspect of the invention relates to a vector comprising said nucleic acid molecule and optionally regulatory sequences for expression in a host cell.

Another aspect of the invention relates to a transgenic host cell comprising said vector.

The present invention also relates to a method for producing a protein, fragment or derivative according to the present invention, comprising the steps:

culturing the host cell according to the present invention in a suitable medium; and
isolating said protein, fragment or derivative from said medium.

Details

Shotgun phage display was used to identify three immunogenic proteins in an isolate (V1) of the DD *Treponema* phylotype closely related to *T. phagedenis*. This phylotype has been indicated in several studies to be a key agent in the pathogenesis of DD (Klitgaard et al. 2008, Nordhoff et al. 2008, Yano et al. 2009). The phage library was selected against antibodies from a rabbit immunized with live bacteria.

A homolog to the well-characterized immunogenic protein TmpA of *T. pallidum* subsp. *pallidum* was identified as well as two proteins without homology to any known spirochetal protein. The complete amino acid sequence of these proteins was predicted from a genomic sequence of V1 generated by 454 Sequencing™. The three specific immunogenic proteins, and their amino acid sequences, are described in SEQ ID NO: 2, 4 and 6.

The proteins, fragments and derivatives according to the first aspect of the invention may be isolated from a culture of the *Treponema* phylotype closely related to *T. phagedenis* strain V1, or, preferably, recombinantly produced as described below.

Western blot has been performed to show that both antibodies from the immunized rabbit as well as naturally infected cattle bind to the recombinantly produced TmpA homolog and the Ttm fragment.

Pilot ELISA runs have been made and a difference in absorbance has been recorded between sera from cattle with and without DD (table 1). There were only a few overlaps between the results in the healthy and the infected group using single antigens (the TmpA homolog or the Ttm fragment) and no overlaps using a combination of the two antigens.

The immunogenic proteins according to the present invention, and active fragments thereof, can be used in vaccines against diseases caused at least in part by the *Treponema* phylotype closely related to *T. phagedenis*, or other *Treponema* spp.

In certain embodiments, the complete proteins are used in vaccines. In certain embodiments only fragments comprising the relevant epitopes are used. In certain embodiments one or more epitopes of one or more proteins are combined in a single molecule and used in a vaccine. The recombinant proteins, derivatives or fragments thereof may be thus used alone or in different combinations or as fusion proteins of the binding epitopes.

Methods

Helper Phage, Bacterial Strains, Growth Conditions, and DNA-Techniques

Phage R408 (Promega) was used as helper phage. *Escherichia coli* TG1 (Δ(lac-proAB) Δ(mcrB-hsdSM)5 ($r_K^- m_K^-$) thi-1 supE [F'traD36 proAB lacI$^q$ZΔM15]; Stratagene) was used as host in all experiments involving phages or phagemids and grown in Luria-Bertani broth (LB) or on Luria-Bertani agar (LA). When appropriate, 50 µg/ml ampicillin ($C_{16}H_{18}N_3O_4SNa$, Roche) was added. Incubations were at 37° C. Chromosomal DNA from *Treponema* sp. strain V1 was used for construction of the phage library. The *Treponema* strain was grown in flasks with FABGS (fastidious anaerobe broth, LAB 71, LabM, Lancashire, UK with 2.0 g D-glucose per liter and 25% fetal calf serum, S 0115, Biochrom AG, Germany) incubated at 37° C., in anaerobic jars on a shaker (90 rpm). Broth cultures were washed three times in isotonic saline (pH 6.3), followed by one wash in phosphate buffered saline (PBS, pH 7.3). The *Treponema* DNA was prepared by conventional phenol-chloroform extraction. Restriction and modification enzymes were from MBI Fermentas AB and used according to manufacturer's instructions. Plasmids were prepared using QIAprep™ Miniprep (QIAGEN).

Immunization and Purification of Polyclonal Antibodies

This part of the study was approved by the ethical committee on animal experiments in Uppsala (C 300/8). A New Zealand white rabbit was immunized subcutaneously with a live culture of *Treponema* sp. strain V1. A dose of approximately $10^9$ bacteria, washed twice and dispensed in a volume of 0.5 ml isotonic saline, was injected twice with 20 days in between. Serum from the final bleed at day 38 post first immunization was used for purification of antibodies (IgG) for this study. Ten ml serum was sterile filtered through a 0.45 μm syringe filter and applied to a 5 ml HiTrap™ Protein G HP column (GE Healthcare). Rabbit IgG was purified according to the manufacturer's instructions using the Ab Buffer Kit (GE Healthcare). Eluates of purified antibodies were desalted using Zeba Spin Desalting columns (Pierce) and stored in PBS at minus 20° C.

Construction of the *Treponema* sp. Phage Display Library and Selection of Binding Phages (Panning)

The phage library was constructed in the pG8SAET phagemid vector. *Treponema* sp. strain V1 chromosomal DNA was fragmented by sonication until the majority of the fragments were between 0.4-1.5 kb in length. The fragments were made blunt-ended by T4 DNA polymerase and T4 DNA kinase treatment and then ligated into SnaB1-digested and dephosphorylated phagemid vector pG8SAET using Ready-To-Go™ T4 DNA ligase tubes (GE Healthcare). The final library was generated by electrotransformation of the ligated material into *E. coli* TG1 cells (2.5 kV, 25 μF, 360Ω), infection with helper phage, and proliferation of phage particles. This procedure yielded $4 \times 10^7$ transformants, considered as unique clones, 86% of which carried an insert, as determined by colony PCR on 14 randomly selected clones. The final library had a titer of $1 \times 10^{11}$ colony forming units per ml.

Phage displaying immunogenic polypeptides were isolated by panning against rabbit anti-*Treponema* sp. strain V1 IgG. Three panning experiments were performed. Microwells (MaxiSorp™, Nalge Nunc International) were coated with Zymed recombinant Protein G (Invitrogen) at a concentration of 10 μg in 200 μl 50 mM sodium carbonate, pH 9.5. Thereafter, the wells were blocked with phosphate buffered saline pH 7.4 with 0.05% Tween 20 (PBS-T). Rabbit anti-*Treponema* sp. strain V1 IgG was added at a concentration of 85 or 215 μg in 200 μl PBS or 100 μl PBS+100 μl crude *E. coli* lysate (for blocking) After washing, 200 μl of the phage library was added. The wells were incubated for 3 h at room temperature, or over night at 2° C., after which they were washed 25 times before phage were eluted by addition of 50 mM Na-citrate/140 mM NaCl pH 2.0. The eluate was immediately neutralised with 2 M Tris-buffer pH 8.0 and used to infect *E. coli* TG1, which were plated on LA-plates with ampicillin (LAamp). In one panning experiment, elution was also carried out by direct infection of TG1 cells added to the well by the bound phages. After incubation overnight, colonies were counted and 100 colonies transferred to an LAamp-plate. These colonies were then transferred to nitrocellulose-filters for screening of E-tag expression using mouse anti-Etag antibodies (GE Healthcare) and secondary horse radish peroxidase-labelled sheep anti-mouse antibodies (GE Healthcare). The remaining colonies were washed off the plates and superinfected with helper phage to make an enriched library/phage stock, which was used in the second enrichment cycle (repanning) according to the same protocol. In total, two repannings were performed. More than 200 E-tag positive colonies were chosen for plasmid preparation and sequence determination of the inserts using primer SAsekv (5'-TAT CTG GTG GCG TAA CAC CTG CT-3', SEQ ID NO: 17). Plasmid DNA was sequenced on a 3730xl DNA Analyzer (Applied Biosystems) at Uppsala Genome Centre and analyzed with the CLC Main Workbench software (CLC bio). Analyses of the inserts revealed nine, nine, and eight overlapping partial sequences, respectively, from three different genes.

Genome Sequencing and Sequence Analysis

The chromosomal DNA of *Treponema* sp. strain V1 was sequenced and assembled at the KTH Genome Center at KTH Royal Institute of Technology, Stockholm, Sweden, using the Genome Sequencer FLX System, with long-read GS FLX Titanium chemistry and the 454 de novo assembler, Newbler (454 Life Sciences, Branford, Conn., USA). An additional De Novo assembly of the reads was made with CLC Genomics Workbench 3 (CLC bio) and for further sequence editing CLC Main Workbench 5 (CLC bio) was used.

The genome sequence was used to predict the full open reading frames and the corresponding amino acid sequences of the three immunogenic proteins. Homology searches were performed using the BLAST algorithm at the National Center for Biotechnology Information. The SignalP 3.0 Server with Gram-positive data was used for prediction of signal peptides. One protein was predicted as a lipoprotein according to Setubal et al. 2006.

Construction of Clones for Protein Expression and Purification

Genomic *Treponema* sp. strain V1 DNA for PCR was prepared with the DNeasy Blood & Tissue Kit (QIAGEN) following the protocol for Gram-negative bacteria. A 50 μl reaction mixture of 5 μl 10×Pfu Buffer with MgSO$_4$ (Fermentas), 0.2 mM of each deoxynucleotide, 0.2 μM of forward and reverse primers as indicated in Table 2, 1.25 U Pfu DNA polymerase (Fermentas) and 50 ng genomic DNA, was prepared. The thermal cycling conditions were 95° C. for 1 min, 30 cycles of 95° C. for 30 s, 50° C. for 30 s, and 72° C. for 3 min and a final extension at 72° C. for 5 min. PCR products were analyzed by agarose gel electrophoresis and purified with the illustra GFX PCR DNA and Gel Band Purification Kit (GE Healthcare). Purified amplicons were digested with either BamHI and XhoI or NdeI and SapI according to the manufacturer's instructions (Fast digest, Fermentas) and purified as described earlier. The digested amplicons were ligated into the respective vector—BamHI and XhoI digested pGEX-6P-1 (bulk GST purification module, GE Healthcare) or NdeI and SapI digested pTXB1 (IMPACT™ Kit, New England BioLabs)—using the ReadyToGo T4DNA Ligase (GE Healthcare). Ligated material were electrotransformed into competent *Escherichia coli* strain BL21(DE3) (GST) or ER2566 (IMPACT) and spread on LA supplemented with ampicillin (final conc. 50 μg/ml). The presence of inserts in a number of colonies was analyzed by PCR using the vector sequencing primers. Clones with a correct size insert were further analyzed by DNA sequencing.

Production of Recombinant Immunogenic *Treponema* Proteins

Commercially available protein expression and purification systems such as the bulk GST purification module (GE Healthcare) or the IMPACT™ Kit (New England BioLabs) were used for production of recombinant immunogenic *Treponema* proteins according to manufacturer's instructions. Recombinant clones were grown at 37° C. in LB media supplemented with ampicillin (final conc. 50 μg/ml). At an optical density (OD$_{600\ nm}$)~0.6, the growth medium was supplemented with IPTG (final konc. 0.3 mM) and the growth temperature shifted to 20° C. After incubation over night the cells were harvested and resuspended in a buffer [20 mM Tris-HCl (pH 8.0), 500 mM NaCl, 0.1 mM EDTA, and 0.05% (v/v) TWEEN20] and lysed by freezing and thawing. After centrifugation, the supernatants were sterile filtrated and applied onto a chitin column. The columns were washed extensively using the same buffer and treated subsequently with cleavage buffer [20 mM Tris-HCl (pH 8.0), 50 mM NaCl, 0.1 mM EDTA, and 30 mM dithiothreitol (DTT)]. The eluted samples containing the antigens were dialysed against phosphate-buffered saline [PBS; 137 mM NaCl, 2.7 mM KCl, 10 mM Na$_2$HPO$_4$, 1.4 mM KH$_2$PO$_4$ (pH 7.4)].

In the GST-glutathione affinity system, according to the procedure described above, after growth, induction and harvest, the *E. coli* cells were suspended in PBS supplemented with TWEEN20, final conc. 0.1% (v/v) (PBST) whereupon the cells were lysed by freezing and thawing. After centrifugation, the supernatant was sterile filtrated and batch purified with Glutathione-sepharose beads. After extensive washing using PBST the fusion protein was eluted with glutathione elution buffer or treated with scissor protease to release the produced protein. Finally, the amounts of antigens obtained were determined using spectrophotometry and the quality analyzed by SDS-PAGE coomassie staining. The proteins were stored finally at −20° C.

Enzyme-Linked Immunosorbant Assays (ELISAs)

Advantages with using purified proteins recombinantly produced in *E. coli* compared to whole cell lysates in an ELISA are the possibilities of large-scale production and optimization of the test (different combinations of proteins, often less background due to higher specificity). Initial ELISA tests were performed with sera from cattle with and without digital dermatitis (DD) and with sera from the immunized rabbit (above). Microplates (PolySorp™, Nalge Nunc International) were coated with recombinant TmpA homolog and/or recombinant tail tape measure protein fragment at a concentration of 2.5 µg and/or 0.31 µg, respectively, in 100 µl 50 mM sodium carbonate, pH 9.5, overnight at 2° C. Wells were washed twice with 400 µl phosphate buffered saline pH 7.4 with 0.05% Tween 20 (PBS-T). Thereafter, the wells were blocked with PBS-T for one hour at room temperature. One hundred µl serum or PBS-T was added to each well. Four dilutions of each serum were used—1:25, 1:50, 1:100, and 1:200. The microplates were incubated at 37° C. for one hour and then washed three times with 400 µl PBS-T. Horse-radish peroxidase conjugated swine-anti rabbit (Dako) and rabbit-anti cow (Dako) antibodies were added to the relevant wells, diluted 1:4000 and 1:500, respectively, and plates were incubated for one hour at 37° C. The wells were washed three times with 400 µl PBS-T after which 100 µl solution consisting of 20 mM tetramethylbenzidine (TMB) mixed 1:20 with 0.1 M potassium citrate/H$_2$O$_2$ (230 µl/l) pH 4.25, was added. The plates were incubated for 10 minutes at room temperature. To stop the reaction 50 µl 10% sulfuric acid was added. Optical density (OD) was measured at 450 nm and the readings were corrected against a sample buffer blank.

Immunomagnetic Separation Using Antibodies

*Treponema* spp. are fastidious organisms that require complex culture media and anaerobic environments for growth. Additionally, samples from cattle claws have a plethora of other bacteria contaminating the cultures. An option to concentrate and purify *Treponema* spp. for culturing and DNA isolation is immunomagnetic separation (Demirkan et al. 1999, Demirkan et al. 2001, Choi et al. 1996). Immunomagnetic beads covalently coated with for example anti-rabbit IgG coupled with rabbit antibodies raised against said immunogenic proteins, derivatives or active fragments thereof can be used for specific separation of the DD *Treponema* phylotype closely related to *T. phagedenis*.

Vaccines

Bacterial proteins stimulating the immune system to antibody production can also be used for vaccine development. Recombinant proteins can be combined with immune-stimulating complexes (ISCOMs) and/or whole cell lysates to increase the immune response in the animal and hence the protection against the disease-causing agent/s.

Further Experiments Performed

Enzyme-Linked Immunosorbant Assay (ELISA)

Materials and methods: The assays were performed with sera from eight dairy cows with acute DD from the herd from which Tpl strain V1 was isolated, two cows from another herd with no known history of DD, and five calves 6-7 months of age. Digital dermatitis diagnosis was made by visual examination. Microplates (PolySorp™, Nalge Nunc International) were coated with recombinant proteins at concentrations of 1 µg/ml TmpA, 0.8 µg/ml Ttm or 0.02 µg/ml PrrA in 100 µl 50 mM sodium carbonate, pH 9.5, overnight at 2° C. Wells were washed twice with PBS-T and blocked with PBS-T for one hour at room temperature. 171 One hundred µl serum diluted 1:100 in PBS-T was added to each well. The microplates were incubated at 37° C. for one hour and then washed with PBS-T. Horse-radish peroxidase (HRP) conjugated rabbit anti-bovine IgG antibodies (Sigma) diluted 1:8000 or monoclonal 22:26 anti-bovine IgG-HRP antibodies (Svanova Biotech AB) diluted 1:4000 were added to the wells and plates were incubated for one hour at 37° C. The wells were washed three times with PBS-T after which 100 µl solution consisting of 1 mM tetramethylbenzidine and 0.006% H2O2 in 0.1 M potassium citrate pH 4.25, was added. The plates were incubated for 10 minutes at room temperature. To stop the reaction 50 µl 10% sulfuric acid was added. Optical density was measured at 450 nm and the readings were subtracted by the optical density of a sample buffer blank giving the corrected optical density (COD).

Figure 1A:
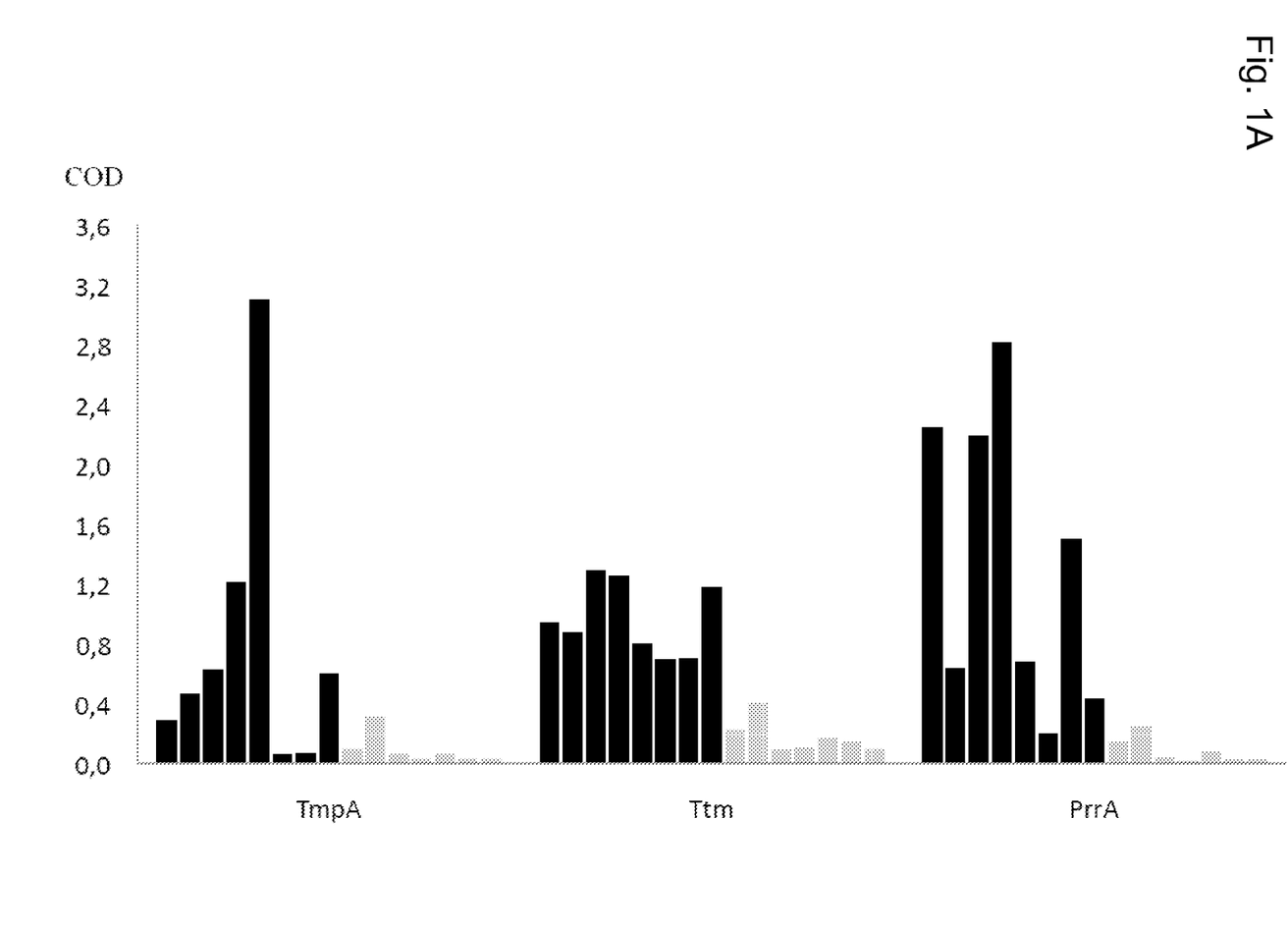
Figure 1B:
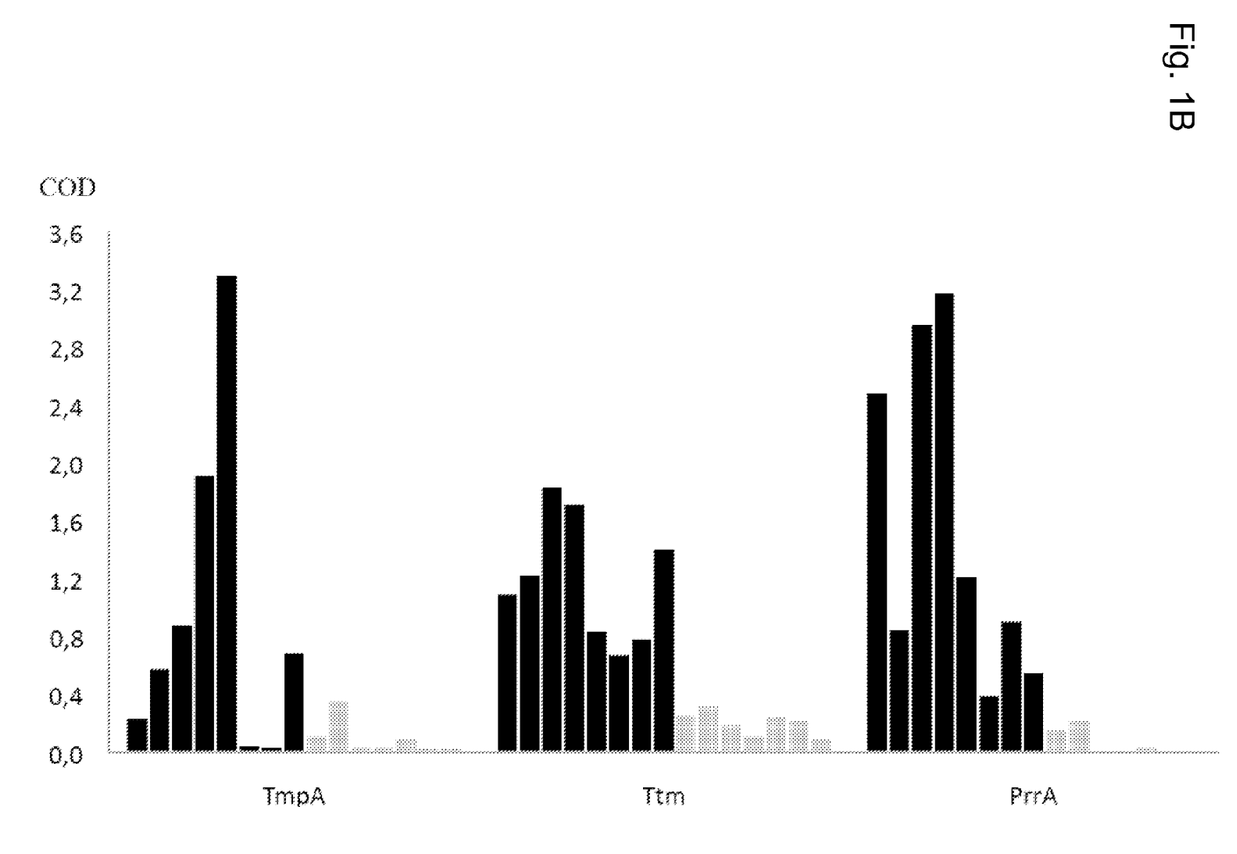

Results: The three immunogenic proteins identified in Tpl strain V1 were produced recombinantly; PrrA as a full-length mature protein from aa+1 relative the cysteine residue of the predicted lipoprotein signal peptide to the last aa before the stop codon (aa:s 22-251), TmpA from aa+7 relative the cystein residue of the predicted lipoprotein signal peptide to the last aa before the stop codon (aa:s 29-344), and Ttm as a partial polypeptide covering aa:s 689-970, which are the aa:s constituting the consensus sequence of the overlapping Ttm sequences from the panning experiments. These proteins/polypeptides were used as antigens in indirect ELISAs where serum samples from cattle with and without DD were analyzed for presence of antibodies against the antigens. Different concentrations of antigen, sera, and secondary antibody were tested in pilot experiments (data not shown). The conditions under which the best discrimination between cattle with and without DD was achieved were used in the final experiment. For the TmpA antigen, the optical density for three samples from cattle with DD was lower than the highest value for the samples from clinically healthy 269 cattle, while the tests with Ttm and PrrA were discriminatory in all cases but one (FIGS. 1A and B).

TABLE 1

Initial ELISA tests of sera from cattle with and without digital dermatitis (DD). Optical density (OD) was measured at 450 nm and the readings were corrected against a sample buffer blank. Sera were diluted 1:100, the concentration of TmpA was 2.5 µg/well and of the putative tail tape measure protein fragment 0.31 µg/well.

| Protein/ protein fragment | Cattle without DD (OD, 450 nm) | | | | | | | Cattle with DD (OD, 450 nm) | | | | | | | | |
|---|---|---|---|---|---|---|---|---|---|---|---|---|---|---|---|---|
| | 1670 | 1680 | 242 | 243 | 245 | 246 | 251 | 5510 | RK | SK | 413 | 571 | 1004 | 2326 | 5542 | 6437 |
| TmpA homolog | 1.23 | 1.06 | 1.28 | 0.91 | 1.31 | 0.75 | 0.73 | 2.55 | 1.25 | 1.7 | 2.18 | 2.26 | 2.44 | 1.82 | 2.96 | 3.15 |
| Putative tail tape measure protein fragment | 1.30 | 1.47 | 1.08 | 1.20 | 1.59 | 0.75 | 0.70 | 2.14 | 1.66 | 1.91 | 1.61 | 1.86 | 2.06 | 1.76 | 1.74 | 1.56 |
| TmpA homolog + putative tail tape measure protein fragment | 1.36 | 1.23 | 0.63 | 0.90 | 0.91 | 0.83 | 0.60 | 2.47 | 1.83 | 1.84 | 1.40 | 1.73 | 2.17 | 1.87 | 2.65 | 2.03 |

TABLE 2

Deoxyoligoribonucleotides

| SEQ ID NO | Name of forward(fwd) and reverse (rev) primer pair | Sequence, 5' to 3' of each primer. Restriction enzyme cleavage sites are indicated in bold. |
|---|---|---|
| 7 | GSTtmpAF1 (fwd) | GGT GGT GGA TCC AAA GCG GAA CAA GAA GCT CA |
| 8 | GSTtmpAR1 (rev) | GGT GGT CTC GAG TCA TTG TAC ACC TCC CTC TA |
| 9 | GSTkallaF1 (fwd) | GGT GGT GGA TCC AAG AAA GAG CTG TTA GAT TT |
| 10 | GSTkallaR1 (rev) | GGT GGT CTC GAG TTA TTT ATC AAT TTC TGC CAA |
| 11 | GSTPGKEEF1 (fwd) | GGT GGT GGA TCC CAA GGT CCA GCT AAC CCC ACA |
| 12 | GSTPGKEER1 (rev) | GGT GGT CTC GAG TTA GAG CTT CTC TAG CAC AAA |
| 13 | ImpactPGKEEF1 (fwd) | GGT GGT CAT ATG CAA GGT CCA GCT AAC CCC ACA |
| 14 | ImpactPGKEER1 (rev) | GGT GGT TGC TCT TCC GCA GAG CTT CTC TAG CAC AAA |
| 15 | ImpactkallaF1 (fwd) | GGT GGT CAT ATG AAG AAA GAG CTG TTA GAT TT |
| 16 | ImpactkallaR1 (rev) | GGT GGT TGC TCT TCC GCA TTT ATC AAT TTC TGC CAA |

REFERENCES

Berry, S. L., Ertze, R. A., Read, D. H., Hird, D. W., 2004, Field evaluation of prophylactic and therapeutic effects of a vaccine against (Papillomatous) Digital Dermatitis of dairy cattle in two Californian dairies. In: Proceedings of the 13th International Symposium and Conference on Lameness in Ruminants, Maribor, Slovenija, p. 147.

Blowey, R. W., Sharp, M. W., 1988. Digital dermatitis in dairy cattle. Vet. Rec. 122, 505-508.

Choi, B. K., Wyss, C., Gobel, U. B., 1996, Phylogenetic analysis of pathogen-related oral spirochetes. J Clin Microbiol. 34, 1922-1925.

Choi, B. K., Nattermann, H., Grund, S., Haider, W., Göbel, U. B., 1997. Spirochetes from digital dermatitis lesions in cattle are closely related to treponemes associated with human periodontitis. Int. J. Syst. Bacteriol. 47, 175-181.

Demirkan, I., Carter, S. D., Hart, C. A., Woodward, M. J., 1999. Isolation and cultivation of a spirochaete from bovine digital dermatitis. Vet. Rec. 145, 497-498.

Demirkan, I., Walker, R. L., Murray, R. D., Blowey, R. W., Carter, S. D., 1999, Serological evidence of spirochaetal infections associated with digital dermatitis in dairy cattle. Vet J. 157, 69-77.

Demirkan, I., Carter, S. D., Winstanley, C., Bruce, K. D., McNair, N. M., Woodside, M., Hart, C. A., 2001, Isolation and characterisation of a novel spirochaete from severe virulent ovine foot rot. J Med. Microbiol. 50, 1061-1068.

Erdile L F, Guy B. OspA lipoprotein of *Borrelia burgdorferi* is a mucosal immunogen and adjuvant Vaccine. 1997 June; 15(9):988-96.

Evans, N. J., Brown, J. M., Demirkan, I., Murray, R. D., Vink, W. D., Blowey, R. W., Hart, C. A., Carter, S. D., 2008. Three unique groups of spirochetes isolated from digital dermatitis lesions in UK cattle. Vet. Microbiol. 30, 141-50.

Gupta, R. B., Fincher, M. G., Bruner, D. W., 1964. A study of the etiology of foot-rot in cattle. Cornell Vet. 54, 66-77.

Hillström, A., Bergsten, C., 2005. Digital dermatitis—a new infectious foot disease in Swedish dairy cattle. Svensk Vet. Tidn. 57, 15-20.

Keil, D. J., Liem, A., Stine, D. L., Anderson, G. A., 2002, Serological and clinical response of cattle to farm specific digital dermatitis bacterins. In: Proceedings of the 12th International Symposium on Lameness in Ruminants, Orlando, Fla., USA, p. 385.

Klitgaard, K., Boye, M., Capion, N., Jensen, T. K., 2008, Evidence of multiple *Treponema* phylotypes involved in bovine digital dermatitis as shown by 16S rRNA gene analysis and fluorescence in situ hybridization. J Clin Microbiol. 46, 3012-3020. Epub 2008 June 3018.

Losinger W. C., 2006. Economic impacts of reduced milk production associated with papillomatous digital dermatitis in dairy cows in the USA. J. Dairy Res. 73, 244-256.

Manske, T., Hultgren, J., Bergsten, C., 2002. Topical treatment of digital dermatitis associated with severe heel-horn erosion in a Swedish dairy herd. Prev. Vet. Med. 53, 215-231.

Moter, A., Leist, G., Rudolph, R., Schrank, K., Choi, B. K., Wagner, M., Göbel, U. B., 1998. Fluorescence in situ hybridization shows spatial distribution of as yet uncultured treponemes in biopsies from digital dermatitis lesions. Microbiology 144, 2459-2467.

Nordhoff, M., Moter, A., Schrank, K., Wieler, L. H., 2008, High prevalence of treponemes in bovine digital dermatitis—a molecular epidemiology. Vet Microbiol. 131, 293-300. Epub 2008 April 2022.

Read, D., Walker, R., 1996. Experimental transmission of papillomatous digital dermatitis (footwarts) in cattle. Vet. pathol. 33, 607.

Read, D., Nordhausen, R., Walker, R. L., 1998. Pathogenesis of experimental papillomatous digital dermatitis (footwarts) in cattle: Bacterial morphotypes associated with early lesion development. In: Lischer C. and Ossent P. (Eds.), Proceedings 10th international symposium on lameness i ruminants, Lucerne, Switzerland, p. 271.

Rodriguez-Lainz, A., Hird, D. W., Carpenter, T. E., Read, D. H., 1996. Case-control study of papillomatous digital dermatitis in Southern California dairy farms. Prev. Vet. Med. 28, 117-131.

Setubal, J. C., Reis, M., Matsunaga, J., Haake, D. A., 2006, Lipoprotein computational prediction in spirochaetal genomes. Microbiol. 152, 113-121.

Trott, D. J., Moeller, M. R., Zuerner, R. L., Goff, J. P., Waters, W. R., Alt, D. P., Walker, R. L., Wannemuehler, M. J., 2003, Characterization of Treponema phagedenis-like spirochetes isolated from papillomatous digital dermatitis lesions in dairy cattle. J Clin Microbiol. 41, 2522-2529.

Vink, W. D., Jones, G., Johnson, W. O., Brown, J., Demirkan, I., Carter, S. D., French, N. P., 2009, Diagnostic assessment without cut-offs: application of serology for the modelling of bovine digital dermatitis infection. Prev Vet Med. 92, 235-248.

Walker, R. L., Read, D. H., Loretz, K. J., Nordhausen, R. W., 1995. Spirochetes isolated from dairy cattle with papillomatous digital dermatitis and interdigital dermatitis. Vet. Microbiol. 47, 343-355.

Walker, R. L., Read, D. H., Loretz, K. J., Hird, D. W., Berry, S. L., 1997, Humoral response of dairy cattle to spirochetes isolated from papillomatous digital dermatitis lesions. Am J Vet Res. 58, 744-748.

Yano, T., Moe, K. K., Yamazaki, K., Ooka, T., Hayashi, T., Misawa, N., 2009, Identification of candidate pathogens of papillomatous digital dermatitis in dairy cattle from quantitative 16S rRNA clonal analysis. Vet Microbiol. 23, 23.

The invention claimed is:

1. A method for detecting the presence of antibodies against proteins from *Treponema* spp. in a sample, comprising the steps:
bringing said sample in contact with an isolated protein having the amino acid sequence of SEQ ID NO:2, SEQ ID NO:4 or SEQ ID NO:6; and
detecting antibodies binding to said protein.

2. A method for in vitro diagnosis of a disease caused by *Treponema* spp. comprising the steps:
obtaining a sample of body fluid or tissue from a subject;
bringing said sample in contact with an isolated protein having the amino acid sequence of SEQ ID NO:2, SEQ ID NO:4 or SEQ ID NO:6; and
detecting in said sample antibodies binding to said protein wherein the presence of antibodies binding to said protein is indicative of a disease caused by *Treponema* spp.

3. The method according to claim 2, wherein said disease is digital dermatitis.

* * * * *

```
                        SEQUENCE LISTING

<160> NUMBER OF SEQ ID NOS: 16

<210> SEQ ID NO 1
<211> LENGTH: 1050
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 1
atggaggtca atgagatgaa attaaaaact ttggtttta gcttatccgc ccttttcctt      60
gtattaggat ttaccggttg taaatctaaa gcacaggcaa aagcggaaca agaagctcaa     120
gaacgaaaag cattgatggc ggaaaatgct aaaatcgaaa aaagattgat gcaagccaaa     180
aatgctgcaa ctgaagcgga agcaaatgta tattatcccg aaaagtttgc acaaattgaa     240
gatttggaaa aacaatcatc ggaagcaaaa gaacaggatg atttaaaaaa agcgaatagc     300
ttgggatctg ctgccgccga caaatacgag acgttggcga ataaaatgaa gatagcgaat     360
caacgctcaa aaattgaagc aaataaactt gcaaaatatg acgaagaaag ctatcgactc     420
ggggaagagg cggagaaaaa gattgacgga ctttatgaaa gcgattccgt tgccgccttg     480
cagacatcaa atgaaagcct tatgtactat aataaggtga tagatgcggg atataagtct     540 cttttcgcaag atgcaaaaaa aacagccgat gatgcaaaag cggcattaac ggcggtaaag     600
gttgccgcga gtttgaaacc ccagcaagag gaagcggatg gaatatatgc taaagctgaa     660
gaagcggaga attccgctca atatgagcaa tcatatggag ggtacacttc tgctgctcaa     720
gcatataacg atttaacaca aataattaag gcaaaacgat tggaagctca aaaggcaatg     780
```

```
caggcggcaa agacaaaaca agaacttttcc gcaaagcttg caaatgaagc ggataaagag    840
agccctctac ctgaaaatgc cgaaggtttt tcaaaagaac cgatagaagt tgaacctctc    900
ccgacagatg tgttaaatgc acctcaagat gaaaagctg aggaaacagt tcccgttgag    960
gaaatgaatg aaaattcttc ggaagaagta aacgggaatg cggaaaaaat tgaatcgact   1020
gaagagccga tagagggagg tgtacaatga                                    1050
```

<210> SEQ ID NO 2
<211> LENGTH: 349
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 2

```
Met Glu Val Asn Glu Met Lys Leu Lys Thr Leu Val Phe Ser Leu Ser
 1               5                  10                  15

Ala Leu Phe Leu Val Leu Gly Phe Thr Gly Cys Lys Ser Lys Ala Gln
            20                  25                  30

Ala Lys Ala Glu Gln Glu Ala Gln Glu Arg Lys Ala Leu Met Ala Glu
        35                  40                  45

Asn Ala Lys Ile Glu Lys Arg Leu Met Gln Ala Lys Asn Ala Ala Thr
    50                  55                  60

Glu Ala Glu Ala Asn Val Tyr Tyr Pro Glu Lys Phe Ala Gln Ile Glu
65                  70                  75                  80

Asp Leu Glu Lys Gln Ser Ser Glu Ala Lys Glu Gln Asp Asp Leu Lys
                85                  90                  95

Lys Ala Asn Ser Leu Gly Ser Ala Ala Asp Lys Tyr Glu Thr Leu
            100                 105                 110

Ala Asn Lys Met Lys Ile Ala Asn Gln Arg Ser Lys Ile Glu Ala Asn
        115                 120                 125

Lys Leu Ala Lys Tyr Asp Glu Glu Ser Tyr Arg Leu Gly Glu Glu Ala
    130                 135                 140

Glu Lys Lys Ile Asp Gly Leu Tyr Glu Ser Asp Ser Val Ala Ala Leu
145                 150                 155                 160

Gln Thr Ser Asn Glu Ser Leu Met Tyr Tyr Asn Lys Val Ile Asp Ala
                165                 170                 175

Gly Tyr Lys Ser Leu Ser Gln Asp Ala Lys Lys Thr Ala Asp Asp Ala
            180                 185                 190

Lys Ala Ala Leu Thr Ala Val Lys Val Ala Ala Ser Leu Lys Pro Gln
        195                 200                 205

Gln Glu Glu Ala Asp Gly Ile Tyr Ala Lys Ala Glu Glu Ala Glu Asn
    210                 215                 220

Ser Ala Gln Tyr Glu Gln Ser Tyr Gly Gly Tyr Thr Ser Ala Ala Gln
225                 230                 235                 240

Ala Tyr Asn Asp Leu Thr Gln Ile Ile Lys Ala Lys Arg Leu Glu Ala
                245                 250                 255

Gln Lys Ala Met Gln Ala Ala Lys Thr Lys Gln Glu Leu Ser Ala Lys
            260                 265                 270

Leu Ala Asn Glu Ala Asp Lys Glu Ser Pro Leu Pro Glu Asn Ala Glu
        275                 280                 285

Gly Phe Ser Lys Glu Pro Ile Glu Val Glu Pro Leu Pro Thr Asp Val
    290                 295                 300
```

Leu Asn Ala Pro Gln Asp Glu Lys Ala Glu Glu Thr Val Pro Val Glu
305                 310                 315                 320

Glu Met Asn Glu Asn Ser Ser Glu Glu Val Asn Gly Asn Ala Glu Lys
            325                 330                 335

Ile Glu Ser Thr Glu Glu Pro Ile Glu Gly Gly Val Gln
            340                 345

<210> SEQ ID NO 3
<211> LENGTH: 3546
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 3

| | | | |
|---|---|---|---|
| atggcgaatg tatcaatagg caatttatat gcatccttaa gtttaaaaag cgaaaagctg | 60 |
| aaaagcggag cgattgaagc tgaaggcgtc atgcgcaagc ttgaaaaaga cattgatgat | 120 |
| ataaaggacg ctattaataa taaacttgcg atgatagggg ctacattgtc cgcaggcgta | 180 |
| acgctgccgc ttactcttat gggaaagagt gcgcttgata ccttctctca atttgagcaa | 240 |
| gccatgcaaa atacttttc cgttatggga gcgacggctt ccgaaatgga atgcttcgt | 300 |
| aaaaaagcgg aagacatggg agctgcgacc cgatttagtg caagccaagc ggcagatgct | 360 |
| ctttatagtt taggctcggc aggacaaagc gcaaccgaag cggcagcaag tcttgacggt | 420 |
| gtattaagct tagcaggagc gacggggagc gatttagcct ttacttcaga aacaataaca | 480 |
| tcaacattat cacagtttaa catggaggct tcaaaagcgt cgcatgtcgc agatgtatac | 540 |
| gcaaaggcaa ttagcaagag ccaagcgaac atgacaaaac tttcgtattc aatgcggtat | 600 |
| gtcgggcctg ttgcatccgg acttgggata agtttagaga cagcaacggc agctttaatg | 660 |
| cgcctttaca ataccggtta cggcggcgag atggcaggta actatcttaa aaacggattg | 720 |
| caaagattag caagcggcgg ggaagacttc aaagcaaaac ttgacgccat cgggcttagt | 780 |
| tatgacgaag taaccctaa aaccaacaac cttgccgaca ttatagaacg cttacgggag | 840 |
| aagcaagtag acgtaacaaa ggcgaatgaa ttattcggag atgcggcagg cggcgcaatg | 900 |
| cttaagctta ttgaaggcgg aggggaagca atacgaacaa tggatgggtt gctgcaatct | 960 |
| tcacacggaa cggcggaaga aatgcagaaa atgcaaaata cttcttttgc aaatacaaaa | 1020 |
| gatgaattgt catcggcgtt tgaggcgtg caaattacgc ttacctctaa tgtaataccg | 1080 |
| gcggttgaca tggtggcgaa ggcatttact aaagtattac agtttgtcaa cgagctgccc | 1140 |
| gttggggtgc aagtagcagg aacgggatta gcgacaatgg cggcagcggc gggaccttta | 1200 |
| ttgcttgttg ccttgagtgt aaagaaaata aaggcggaaa tggcagccct caatgttacg | 1260 |
| atgatgtcta atccgatatt ccttatcggc acggcaattg cggcgggac ggctttagca | 1320 |
| ttaggagcga ttgcacaaat acgaaaagca atgatgatt atatacacag tgcaaaacgg | 1380 |
| agtattgatg atattcggaa aatgcaagat aacgcccttg ctgaaggtaa taggggcgg | 1440 |
| aagattaact cacttttgga tgagtatgaa acgctcaaga ataaacaac aagaacggcc | 1500 |
| gatgaacaag ctcgatataa tcaactgttg gcagaattac aagagcttgt tcctgatgtt | 1560 |
| gtaacaaaac tgaacgcgca aggggaagca tttattgaga atgcggagaa agctcgagag | 1620 |
| gcggcacggc agcaattaga aacagagaaa gcattaaacg atatggcact tgtaacgaca | 1680 |
| agagcaaaag cagaacatgc cgaagcggtt attgcaaaat acaaaaataa accgaaagag | 1740 |

```
ctgcaagcgc agttaaaaat tgaaacggaa aatgtaaaag cggcaacatt actatatcag    1800
cagatacaag caaaatacga agagtttaaa catttgcaag aagcgggaag agaaaccgcc    1860
gccgcaaaaa taagagaaga aattcagcat ctgtatcttt caaataacgg ggtacaagcg    1920
gaaggcgggg tatgggatta tggcaatgta aaaaaaatgg taaaagcgtt tgaaaaacat    1980
cttaatacgg ttactggtaa acagcagaaa acgctgagat tatatgagag cattaaaaac    2040
gctgtagaag aaaatattgc agcaaagaaa gagctgttag atttagaagc aaggagcctt    2100
gcaattgcaa aagctcaagg ggaattatca gaagaagcaa gcaaaaaaga acagcaaaa     2160 acacgtcagc agcacgcaga tacttcttgg gacgaatatg agacaagaaa aaaacgatgg    2220 gaaaagaaa agaaagaagc ggtcttttta ggacgggaat tgatgaagt tggtaagaaa      2280 atagaattct gcaagcagaa aataagcaat ctgttacatc ttaacgctgc cgatgttgca    2340
gatggagttt ttgcgctcaa ttcaaaagag cttaaaaaat taaagaaaga gctggatacc    2400
cttcttaagc tacagggaaa aaataaaaag aatggcagcg gcggcgaaaa atcaaaagat    2460
ttgcaggcac acattgatga gcttgatagt tactatcgca agcgtatttc aatggcaaaa    2520
gaatacggct tgaatgaagc aaaagaaaca gaaaaatggt tgaaagaacg aaaggcgcta    2580
ttagataaat acaataatga aaaagaactc cggaaaaaag aagcaggggg aagcggtata    2640
actgttggag atgaaaaaaa acgaacagag tttttaggtt atgccgattt tacaaaatat    2700
cttaatgagc aaaaagaatt acaaaagaa ctggataaaa caagagaaaa tatagaaaag    2760
acgaaagcat tgcttgcgtc aaagggaaa gaccttaccc cgaacgaaag gcgtgcagca    2820
aaagattatt tagaagactt acaagaaaaa gcaaacaagt tagagataga actaaaacaa    2880 tctcaatta cattggcaga aattgataaa actttagaag ctattgagaa ttgtaacaag     2940
tctgattttg aactaaagct tattaatatc gaaaagaaa aagagcgatt actgcaagtc     3000
atagatgagg caagaaaagc agggaaaata agcgaagaag aagcggaaaa agcgaagaaa    3060
aaagttcaag aaaaacaaa aaaggacaag caaggcgagt cagttaaaaa tgctgatcca    3120
tacgtaaagg gagcaattgg cattgcaaat gcgattgctg atgttatcgc tgatgcgatt    3180
gaaaaaggtg gcgttgacgg tcttaccgct atagcagcag caggagagat tatcggtcaa    3240
attggggata tggtcggaaa ctctgtggca aaagctgtct tgggggcaac aagtgcggta    3300
gtcggaataa ctacaaaaat tatgggcgca atcaggcgaa agaatgctgc atattcagca    3360
gaacaaagag agaaaatgaa aaattttaat cagaaagtac aagaaggaat agaaaaaaat    3420
atccgcagag caagtgaaat cgcaggggac gtgcctaaaa cactggcaaa agcttttagc    3480
ggaaaaaaac tgtcaatcga tagtatttt gatagtcaat cagtggaact acaaaagaaa    3540
aaatag                                                              3546
```

<210> SEQ ID NO 4
<211> LENGTH: 1181
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 4

```
Met Ala Asn Val Ser Ile Gly Asn Leu Tyr Ala Ser Leu Ser Leu Lys
1               5                   10                  15

Ser Glu Lys Leu Lys Ser Gly Ala Ile Glu Ala Glu Gly Val Met Arg
            20                  25                  30
```

```
Lys Leu Glu Lys Asp Ile Asp Asp Ile Lys Asp Ala Ile Asn Asn Lys
             35                  40                  45
Leu Ala Met Ile Gly Ala Thr Leu Ser Ala Gly Val Thr Leu Pro Leu
 50                  55                  60
Thr Leu Met Gly Lys Ser Ala Leu Asp Thr Phe Ser Gln Phe Glu Gln
 65                  70                  75                  80
Ala Met Gln Asn Thr Phe Ser Val Met Gly Ala Thr Ala Ser Glu Met
                 85                  90                  95
Glu Met Leu Arg Lys Lys Ala Glu Asp Met Gly Ala Ala Thr Arg Phe
                100                 105                 110
Ser Ala Ser Gln Ala Ala Asp Ala Leu Tyr Ser Leu Gly Ser Ala Gly
                115                 120                 125
Gln Ser Ala Thr Glu Ala Ala Ala Ser Leu Asp Gly Val Leu Ser Leu
                130                 135                 140
Ala Gly Ala Thr Gly Ser Asp Leu Ala Phe Thr Ser Glu Thr Ile Thr
145                 150                 155                 160
Ser Thr Leu Ser Gln Phe Asn Met Glu Ala Ser Lys Ala Ser His Val
                165                 170                 175
Ala Asp Val Tyr Ala Lys Ala Ile Ser Lys Ser Gln Ala Asn Met Thr
                180                 185                 190
Lys Leu Ser Tyr Ser Met Arg Tyr Val Gly Pro Val Ala Ser Gly Leu
                195                 200                 205
Gly Ile Ser Leu Glu Thr Ala Thr Ala Ala Leu Met Arg Leu Tyr Asn
                210                 215                 220
Thr Gly Tyr Gly Gly Glu Met Ala Gly Asn Tyr Leu Lys Asn Gly Leu
225                 230                 235                 240
Gln Arg Leu Ala Ser Gly Gly Glu Asp Phe Lys Ala Lys Leu Asp Ala
                245                 250                 255
Ile Gly Leu Ser Tyr Asp Glu Val Asn Pro Lys Thr Asn Asn Leu Ala
                260                 265                 270
Asp Ile Ile Glu Arg Leu Arg Glu Lys Gln Val Asp Val Thr Lys Ala
                275                 280                 285
Asn Glu Leu Phe Gly Asp Ala Ala Gly Gly Ala Met Leu Lys Leu Ile
                290                 295                 300
Glu Gly Gly Gly Glu Ala Ile Arg Thr Met Asp Gly Leu Leu Gln Ser
305                 310                 315                 320
Ser His Gly Thr Ala Glu Glu Met Gln Lys Met Gln Asn Thr Ser Phe
                325                 330                 335
Ala Asn Thr Lys Asp Glu Leu Ser Ser Ala Phe Glu Ala Val Gln Ile
                340                 345                 350
Thr Leu Thr Ser Asn Val Ile Pro Ala Val Asp Met Val Ala Lys Ala
                355                 360                 365
Phe Thr Lys Val Leu Gln Phe Val Asn Glu Leu Pro Val Gly Val Gln
                370                 375                 380
Val Ala Gly Thr Gly Leu Ala Thr Met Ala Ala Ala Gly Pro Leu
385                 390                 395                 400
Leu Leu Val Ala Leu Ser Val Lys Lys Ile Lys Ala Glu Met Ala Ala
                405                 410                 415
Leu Asn Val Thr Met Met Ser Asn Pro Ile Phe Leu Ile Gly Thr Ala
                420                 425                 430
Ile Ala Ala Gly Thr Ala Leu Ala Leu Gly Ala Ile Ala Gln Ile Arg
                435                 440                 445
Lys Ala Asn Asp Asp Tyr Ile His Ser Ala Lys Arg Ser Ile Asp Asp
```

-continued

```
            450                 455                 460
Ile Arg Lys Met Gln Asp Asn Ala Leu Ala Glu Gly Asn Lys Gly Arg
465                 470                 475                 480

Lys Ile Asn Ser Leu Leu Asp Glu Tyr Glu Thr Leu Lys Asn Lys Thr
                    485                 490                 495

Thr Arg Thr Ala Asp Glu Gln Ala Arg Tyr Asn Gln Leu Leu Ala Glu
                500                 505                 510

Leu Gln Glu Leu Val Pro Asp Val Val Thr Lys Leu Asn Ala Gln Gly
            515                 520                 525

Glu Ala Phe Ile Glu Asn Ala Glu Lys Ala Arg Glu Ala Ala Arg Gln
530                 535                 540

Gln Leu Glu Thr Glu Lys Ala Leu Asn Asp Met Ala Leu Val Thr Thr
545                 550                 555                 560

Arg Ala Lys Ala Glu His Ala Glu Ala Val Ile Ala Lys Tyr Lys Asn
                565                 570                 575

Lys Pro Lys Glu Leu Gln Ala Gln Leu Lys Ile Glu Thr Glu Asn Val
                580                 585                 590

Lys Ala Ala Thr Leu Leu Tyr Gln Gln Ile Gln Ala Lys Tyr Glu Glu
                595                 600                 605

Phe Lys His Leu Gln Glu Ala Gly Arg Glu Thr Ala Ala Ala Lys Ile
610                 615                 620

Arg Glu Glu Ile Gln His Leu Tyr Leu Ser Asn Asn Gly Val Gln Ala
625                 630                 635                 640

Glu Gly Gly Val Trp Asp Tyr Gly Asn Val Lys Lys Met Val Lys Ala
                645                 650                 655

Phe Glu Lys His Leu Asn Thr Val Thr Gly Lys Gln Gln Lys Thr Leu
                660                 665                 670

Arg Leu Tyr Glu Ser Ile Lys Asn Ala Val Glu Glu Asn Ile Ala Ala
                675                 680                 685

Lys Lys Glu Leu Leu Asp Leu Glu Ala Arg Ser Leu Ala Ile Ala Lys
690                 695                 700

Ala Gln Gly Glu Leu Ser Glu Glu Ala Ser Lys Lys Glu Thr Ala Lys
705                 710                 715                 720

Thr Arg Gln Gln His Ala Asp Thr Ser Trp Asp Glu Tyr Glu Thr Arg
                725                 730                 735

Lys Lys Arg Trp Glu Lys Glu Lys Lys Glu Ala Val Phe Leu Gly Arg
                740                 745                 750

Glu Phe Asp Glu Val Gly Lys Lys Ile Glu Phe Leu Gln Ala Glu Ile
                755                 760                 765

Ser Asn Leu Leu His Leu Asn Ala Ala Asp Val Ala Asp Gly Val Phe
770                 775                 780

Ala Leu Asn Ser Lys Glu Leu Lys Lys Leu Lys Lys Glu Leu Asp Thr
785                 790                 795                 800

Leu Leu Lys Leu Gln Gly Lys Asn Lys Asn Gly Ser Gly Gly Glu
                805                 810                 815

Lys Ser Lys Asp Leu Gln Ala His Ile Asp Glu Leu Asp Ser Tyr Tyr
                820                 825                 830

Arg Lys Arg Ile Ser Met Ala Lys Glu Tyr Gly Leu Asn Glu Ala Lys
                835                 840                 845

Glu Thr Glu Lys Trp Leu Lys Glu Arg Lys Ala Leu Leu Asp Lys Tyr
                850                 855                 860

Asn Asn Glu Lys Glu Leu Arg Lys Lys Glu Ala Gly Gly Ser Gly Ile
865                 870                 875                 880
```

```
Thr Val Gly Asp Glu Lys Lys Arg Thr Glu Phe Leu Gly Tyr Ala Asp
            885                 890                 895

Phe Thr Lys Tyr Leu Asn Glu Gln Lys Glu Leu Gln Lys Glu Leu Asp
        900                 905                 910

Lys Thr Arg Glu Asn Ile Glu Lys Thr Lys Ala Leu Leu Ala Ser Lys
    915                 920                 925

Gly Lys Asp Leu Thr Pro Asn Glu Arg Arg Ala Ala Lys Asp Tyr Leu
930                 935                 940

Glu Asp Leu Gln Glu Lys Ala Asn Lys Leu Glu Ile Glu Leu Lys Gln
945                 950                 955                 960

Ser Gln Phe Thr Leu Ala Glu Ile Asp Lys Thr Leu Ala Ile Glu
            965                 970                 975

Asn Cys Asn Lys Ser Asp Phe Glu Leu Lys Leu Ile Asn Ile Glu Lys
            980                 985                 990

Glu Lys Glu Arg Leu Leu Gln Val Ile Asp Glu Ala Lys Lys Ala Gly
            995                 1000                1005

Lys Ile Ser Glu Glu Glu Ala Glu Lys Ala Lys Lys Val Gln
    1010                1015                1020

Glu Lys Thr Lys Lys Asp Lys Gln Gly Glu Ser Val Lys Asn Ala
    1025                1030                1035

Asp Pro Tyr Val Lys Gly Ala Ile Gly Ile Ala Asn Ala Ile Ala
    1040                1045                1050

Asp Val Ile Ala Asp Ala Ile Glu Lys Gly Gly Val Asp Gly Leu
    1055                1060                1065

Thr Ala Ile Ala Ala Ala Gly Glu Ile Ile Gly Gln Ile Gly Asp
    1070                1075                1080

Met Val Gly Asn Ser Val Ala Lys Ala Val Leu Gly Ala Thr Ser
    1085                1090                1095

Ala Val Val Gly Ile Thr Thr Lys Ile Met Gly Ala Ile Arg Arg
    1100                1105                1110

Lys Asn Ala Ala Tyr Ser Ala Glu Gln Arg Glu Lys Met Lys Asn
    1115                1120                1125

Phe Asn Gln Lys Val Gln Glu Gly Ile Glu Lys Asn Ile Arg Arg
    1130                1135                1140

Ala Ser Glu Ile Ala Gly Asp Val Pro Lys Thr Leu Ala Lys Ala
    1145                1150                1155

Phe Ser Gly Lys Lys Leu Ser Ile Asp Ser Ile Phe Asp Ser Gln
    1160                1165                1170

Ser Val Glu Leu Gln Lys Lys Lys
    1175                1180

<210> SEQ ID NO 5
<211> LENGTH: 756
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 5
atgaaaaagt tacgttttat tagctttgcc atattggcaa cagcattgat tgttgtatct      60
tgccaaggtc cagctaaccc cacaaaagaa cctggcaatg ttcagaaagc tgaggagaaa     120
aaaccagagg tgaaagatcc aaaagctgag gagaaaaaac cagaggtgaa agatccaaaa     180
gctgaggaga aaaaaccaga ggagacatct ccaggtacag aaaaaccagt agctccaggt     240
```

```
aaagaagagc caggtaaaga agagccaggt aaagaagagc caggtaaaga agagccaggt    300
aaagaagagc caggtaaaga agagccaggt aaagaagagc ttcatgagtt tattggcgag    360
ctttgtgaaa tagcggaaga ggaagaaatg cctgctgacg aagttagtcg ttgggttgaa    420
ctagcgcaga aggattttga acaattcggc gtcaaaattg tggacaaaga agctgatcag    480
ccaattaaaa agggtgccag tgaagaagat cttaaaaaac gctttgtgct agagaaagat    540
ccaaatgctg agcttcatgg gtttattggc gagctttgtg aaatagcgga gaggaagaa     600 atgcctgctg acgaagttag tcgttgggtt gaactagcgc aggaggattt tgaacaattc    660
ggcgtcaaaa ttgtggacaa agaagctgat cagccaatta aaaagggtgc cagtgaagaa    720
gatcttaaaa aacgctttgt gctagagaag ctctaa                              756
```

<210> SEQ ID NO 6
<211> LENGTH: 251
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Treponema phagedenis-like

<400> SEQUENCE: 6

```
Met Lys Lys Leu Arg Phe Ile Ser Phe Ala Ile Leu Ala Thr Ala Leu
1               5                   10                  15

Ile Val Val Ser Cys Gln Gly Pro Ala Asn Pro Thr Lys Glu Pro Gly
            20                  25                  30

Asn Val Gln Lys Ala Glu Glu Lys Pro Glu Val Lys Asp Pro Lys
        35                  40                  45

Ala Glu Glu Lys Lys Pro Glu Val Lys Asp Pro Lys Ala Glu Glu Lys
    50                  55                  60

Lys Pro Glu Glu Thr Ser Pro Gly Thr Glu Lys Pro Val Ala Pro Gly
65                  70                  75                  80

Lys Glu Glu Pro Gly Lys Glu Glu Pro Gly Lys Glu Glu Pro Gly Lys
                85                  90                  95

Glu Glu Pro Gly Lys Glu Glu Pro Gly Lys Glu Glu Pro Gly Lys Glu
            100                 105                 110

Glu Leu His Glu Phe Ile Gly Glu Leu Cys Glu Ile Ala Glu Glu Glu
        115                 120                 125

Glu Met Pro Ala Asp Glu Val Ser Arg Trp Val Glu Leu Ala Gln Lys
    130                 135                 140

Asp Phe Glu Gln Phe Gly Val Lys Ile Val Asp Lys Glu Ala Asp Gln
145                 150                 155                 160

Pro Ile Lys Lys Gly Ala Ser Glu Glu Asp Leu Lys Lys Arg Phe Val
                165                 170                 175

Leu Glu Lys Asp Pro Asn Ala Glu Leu His Gly Phe Ile Gly Glu Leu
            180                 185                 190

Cys Glu Ile Ala Glu Glu Glu Met Pro Ala Asp Glu Val Ser Arg
        195                 200                 205

Trp Val Glu Leu Ala Gln Glu Asp Phe Glu Gln Phe Gly Val Lys Ile
    210                 215                 220

Val Asp Lys Glu Ala Asp Gln Pro Ile Lys Lys Gly Ala Ser Glu Glu
225                 230                 235                 240

Asp Leu Lys Lys Arg Phe Val Leu Glu Lys Leu
                245                 250
```

<210> SEQ ID NO 7
<211> LENGTH: 32
<212> TYPE: DNA
<213> ORGANISM: Artificial Sequence
<220> FEATURE:
<223> OTHER INFORMATION: Synthetic

<400> SEQUENCE: 7
ggtggtggat ccaaagcgga acaagaagct ca                          32

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
ggtggtctcg agtcattgta cacctccctc ta                          32

<210> SEQ ID NO 9
<211> LENGTH: 32
<212> TYPE: DNA
<213> ORGANISM: Artificial Sequence
<220> FEATURE:
<223> OTHER INFORMATION: Synthetic

<400> SEQUENCE: 9
ggtggtggat ccaagaaaga gctgttagat tt                          32

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
ggtggtctcg agttatttat caatttctgc caa                         33

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
ggtggtggat cccaaggtcc agctaacccc aca                         33

<210> SEQ ID NO 12
<211> LENGTH: 33
<212> TYPE: DNA
<213> ORGANISM: Artificial Sequence
<220> FEATURE:
<223> OTHER INFORMATION: Synthetic

<400> SEQUENCE: 12
ggtggtctcg agttagagct tctctagcac aaa                         33

<210> SEQ ID NO 13
<211> LENGTH: 33
<212> TYPE: DNA
<213> ORGANISM: Artificial Sequence
<220> FEATURE:
<223> OTHER INFORMATION: Synthetic

```
<400> SEQUENCE: 13
ggtggtcata tgcaaggtcc agctaacccc aca                          33

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
ggtggttgct cttccgcaga gcttctctag cacaaa                       36

<210> SEQ ID NO 15
<211> LENGTH: 32
<212> TYPE: DNA
<213> ORGANISM: Artificial Sequence
<220> FEATURE:
<223> OTHER INFORMATION: Synthetic

<400> SEQUENCE: 15
ggtggtcata tgaagaaaga gctgttagat tt                           32

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
ggtggttgct cttccgcatt tatcaatttc tgccaa                       36
```